(12) United States Patent
Wendenburg

(10) Patent No.: US 10,478,218 B2
(45) Date of Patent: Nov. 19, 2019

(54) SCALPEL HOLDER

(71) Applicant: HELMUT ZEPF MEDIZINTECHNIK GMBH, Seitingen-Oberflacht (DE)

(72) Inventor: Frank Wendenburg, Muehlheim (DE)

(73) Assignee: HELMUT ZEPF MEDIZINTECHNIK GMBH, Seitingen-Oberflacht (DE)

( * ) Notice: Subject to any disclaimer, the term of this patent is extended or adjusted under 35 U.S.C. 154(b) by 249 days.

(21) Appl. No.: 14/183,992

(22) Filed: Feb. 19, 2014

(65) Prior Publication Data

US 2014/0257354 A1 Sep. 11, 2014

(30) Foreign Application Priority Data

Feb. 25, 2013 (DE) .................... 20 2013 100 819 U

(51) Int. Cl.
*A61B 17/3213* (2006.01)
*A61B 17/3217* (2006.01)

(52) U.S. Cl.
CPC ...... *A61B 17/3213* (2013.01); *A61B 17/3217* (2013.01)

(58) Field of Classification Search
CPC .................. A61B 17/3213; A61B 17/3217
USPC .................... 606/167, 170; 30/329, 339, 162
See application file for complete search history.

(56) References Cited

U.S. PATENT DOCUMENTS

| | | | |
|---|---|---|---|
| 774,812 A | 11/1904 | Wurts | |
| 2,039,443 A * | 5/1936 | Ogden | 30/339 |
| 2,330,639 A * | 9/1943 | Testi | 30/40.2 |
| 2,521,032 A * | 9/1950 | Becker | 30/129 |
| 5,312,429 A * | 5/1994 | Noack | 606/167 |
| 5,423,843 A | 6/1995 | Werner | |
| 5,662,669 A * | 9/1997 | Abidin | A61B 17/3213 30/151 |
| 5,752,968 A * | 5/1998 | Jolly et al. | 606/167 |
| 6,022,364 A | 2/2000 | Flumene et al. | |

(Continued)

FOREIGN PATENT DOCUMENTS

| | | |
|---|---|---|
| DE | 1144 437 B | 9/1963 |
| DE | 40 40 909 A1 | 12/1990 |

OTHER PUBLICATIONS

Office Action issued by Chinese Patent Office for parallel application No. 201410063132.9, dated Mar. 23, 2016.

(Continued)

*Primary Examiner* — Andrea L Wellington
*Assistant Examiner* — Fernando A Ayala
(74) *Attorney, Agent, or Firm* — William Gray Mitchell

(57) ABSTRACT

A scalpel holder, having a grip piece with a longitudinal direction and a blade holder which is connected to the grip piece and which functions to receive a scalpel blade and hold the same fixed, wherein the grip piece has a slider guide which runs substantially in the longitudinal direction of the grip piece for the purpose of receiving a slider, wherein the same can be movably guided in said slider guide toward the blade holder, and the slider guide is arranged on the grip piece in such a manner that the end piece, the same designed with a wedge shape, of the slider which is guided in the slider guide in the direction of the blade holder slides past the scalpel blade while lifting the same out of the blade holder.

16 Claims, 3 Drawing Sheets

(56) References Cited

U.S. PATENT DOCUMENTS

| | | | |
|---|---|---|---|
| 6,085,423 A * | 7/2000 | Marifone | 30/162 |
| 7,748,124 B1 | 7/2010 | Bell et al. | |
| 8,156,653 B2 | 4/2012 | Austria | |
| 8,205,340 B2 | 6/2012 | Austria | |
| 2004/0163264 A1* | 8/2004 | Simonz | 30/517 |
| 2005/0065541 A1* | 3/2005 | Abidin et al. | 606/167 |

OTHER PUBLICATIONS

Correspondence and amendment from Applicant to German Patent and Trademark Office (GPTO) for parallel application No. 102014101658.0, dated May 15, 2017.

Notice of Grant issued by Chinese Patent Office for parallel application No. 2014 1006 3132.9, dated May 3, 2017, granting independent claim containing features of original US claims 1 and 3.

Decision of Grant issued by the German Patent and Trademark Office for parallel application No. 102014101658.0, dated May 31, 2017, granting independent claim containing features of original US claims 1 and 3.

Office Action issued by German Patent Office for parallel application No. 10 2014 101 658.0, dated Jun. 1, 2016.

Office Action issued by Chinese Patent Office for parallel application No. 2014 1006 3132.9, dated Dec. 5, 2016.

* cited by examiner

SCALPEL HOLDER

CROSS REFERENCE TO RELATED APPLICATIONS

This patent application claims priority German Patent Application 20 2013 100 819.2, filed on Feb. 25, 2013.

STATEMENT REGARDING FEDERALLY SPONSORED RESEARCH OR DEVELOPMENT

No federal government funds were used in researching or developing this invention.

NAMES OF PARTIES TO A JOINT RESEARCH AGREEMENT

Not applicable.

SEQUENCE LISTING INCLUDED AND INCORPORATED BY REFERENCE HEREIN

Not applicable.

BACKGROUND

Field of the Invention

The invention relates to a scalpel holder.

Background of the Invention

The current state of knowledge is as follows.

Scalpels are known as instruments for cutting organic tissue in the field of surgery and the practice of dentistry. A differentiation is made between disposable scalpels—meaning scalpels which are intended to be used one time, wherein the scalpel blade is fixed to a grip piece—and scalpels with a detachable blade—particularly disposable blades—wherein the blade is connected to a grip piece, termed a scalpel grip.

Disposable scalpels are entirely discarded following use, whereas scalpels with disposable blades have grip pieces which are used multiple times, while the disposable blade is disposed of. In surgical and dental practice, the use of scalpel holders with disposable blades is most commonly preferred.

In the case of scalpels with detachable blades, the sterile disposable blades are removed from their sterile packaging and placed in the sterilized blade holder. The disposable blade in this case is generally packaged in such a manner that the disposable blade can be grabbed from the packaging when the same has been opened on one side, and can be placed in the blade holder. The risk of injury in this placement procedure is minimal, because the sufficiently thick disposable blade packaging surrounds the cutting edge of the scalpel blade during the placement procedure, thereby protecting the person who carries out the placement of the blade from an accidental cutting injury caused by the cutting edge of the scalpel blade. Even if a cutting injury would occur, in this case it would be a so-called sterile injury, because the scalpel blade is in a sterile packaging, and therefore the risk of infection is very manageable. In addition, the blade holder does not transmit any additional germs into the injured tissue if it is sterilized.

However, the removal of a disposable blade, which has already been used, from the blade holder, can be problematic. The risk of injury in this case is very high because the removal of the disposable blade fixed on the blade holder is a more complicated process than the placement of the disposable blade, and the sharp cutting edge of the disposable blade lies exposed. In addition, the already used disposable blade is contaminated with germs, and can no longer be used again, because it has become blunt as a result of use. For this reason, it must be exchanged following use. The removal of the disposable blade must not be carried out by hand for these reasons, and rather requires the use of an additional auxiliary means.

DE 4 040 909 A1 discloses a device for the purpose of exchanging blades, in the form of a housing which has an insertion opening for the grip part of a scalpel for the blade of the scalpel, said blade being inserted into the guide slot of a narrow front part of the grip part, as well as means for pressing out the end region of the blade which faces the grip part, from the front part of the scalpel, and means for the temporary holding of the pressed-out blade during the removal of the grip part. The housing in this case contains a channel which proceeds from the insertion opening and which receives a scalpel with its front part, which holds a blade, said channel having a contact region for the scalpel front part on its base. The channel is bounded near the insertion opening by limit means, which are raised above the base area, for the blade end, pressed out by the scalpel front part. At least one presser element is arranged in the housing, lying opposite the channel base, and oriented toward the blade, wherein the blade can be pressed out of the scalpel front part lying on the channel base by means of the presser element. The risk of injury using this device should be ruled out as a result of the fact that the sharp blade and the scalpel front part are entirely received inside the channel of the housing during the removal of the grip part.

In this known device, there is the disadvantage, on the one hand, that both hands must be used to remove the blade, and on the other hand, that a box with a relatively difficult removal mechanism which must be actuated via a press button is required for the removal of the blade from the blade holder. If the mechanism for the removal of the blade jams or stops functioning, no further blades can be removed from the blade holders. A third disadvantage is, finally, that a malfunction of this device leads to a particularly high risk of injury, particularly if, by way of example, an attempt is made to separate the box from the scalpel holder by force under the assumption that the blade has already been removed.

The problem addressed by the invention is therefore that of creating a device for changing blades in surgical scalpels, which ensures safe manipulation with a simple construction, and which particularly can be actuated safely using one hand.

BRIEF SUMMARY OF THE INVENTION

In a preferred embodiment, a scalpel holder, having a grip piece with a longitudinal direction and a blade holder which is connected to the grip piece and which functions to receive a scalpel blade and hold the same fixed, wherein the grip piece has a slider guide which runs substantially in the longitudinal direction of the grip piece, wherein a slider received in said slider guide is movably guided in the same, wherein the slider has a slider rod and a push rod which are connected to each other in a fixed manner, and the push rod furthermore has an end piece with a wedge-shaped design for the purpose of lifting out a scalpel blade fastened on the blade holder, wherein the slider guide is arranged on the grip piece in such a manner that the end piece of the slider guided in the slider guide in the direction of the blade holder slides past the scalpel blade while lifting the same out of the blade holder.

In another preferred embodiment, the scalpel holder as disclosed, wherein the slider rod is designed as a single piece together with the push rod.

In another preferred embodiment, the scalpel holder as disclosed, wherein the push rod has an edge region constructed on the blunt end of the wedge-shaped end piece for the purpose of pushing out the scalpel blade which has been lifted out of the blade holder.

In another preferred embodiment, the scalpel holder as disclosed, wherein the edge region, the same functioning to push off the scalpel blade which has been lifted out of the blade holder, is arranged on the push rod in such a manner that it, while contacting a narrow side of the scalpel blade, pushes off the scalpel blade from the blade holder, said scalpel blade having been lifted off, when the slider is further guided in the direction of the blade holder.

In another preferred embodiment, the scalpel holder as disclosed, wherein the slider guide is designed as a single piece together with the grip piece.

In another preferred embodiment, the scalpel holder as disclosed, wherein the grip piece is designed as a single piece together with the blade holder.

In another preferred embodiment, the scalpel holder as disclosed, wherein the slider has an actuating region, for example in the form of an actuating element arranged laterally or proximally on the slider, for the purpose of actuating the slider.

In another preferred embodiment, the scalpel holder as disclosed, wherein the slider has a return spring.

In another preferred embodiment, the scalpel holder as disclosed, wherein the return spring is arranged around the slider rod or around a grip piece fastened to the slider.

In another preferred embodiment, the scalpel holder as disclosed, wherein the grip piece is guided in a guide sleeve, and held in the same in a movable manner, said guide sleeve being connected to the grip piece and preferably configured with a bore hole passing through the same, and the return spring is arranged sitting atop the guide sleeve.

In another preferred embodiment, the scalpel holder as disclosed, wherein the grip piece is hollow, and the slider guide is arranged running inside of the grip piece.

In another preferred embodiment, the scalpel holder as disclosed, wherein the grip piece has a first passage on its distal end, and a second passage on its proximal end, for the purpose of guiding the slider through the same.

In another preferred embodiment, the scalpel holder as disclosed, wherein a part of the slider projects from the rear end of the grip piece, and forms the actuating region of the slider.

In another preferred embodiment, the scalpel holder as disclosed, wherein the grip piece has at least two grip piece parts, which can be connected to each other.

In another preferred embodiment, the scalpel holder as disclosed, wherein the at least two grip piece parts are connected to each other by means of bolted connections, plug connections, or bayonet connections, in a detachable manner.

In another preferred embodiment, the scalpel holder as disclosed, wherein the slider has an arrester to protect against unintentional actuation of the slider.

DETAILED DESCRIPTION OF THE INVENTION

Figure 1:
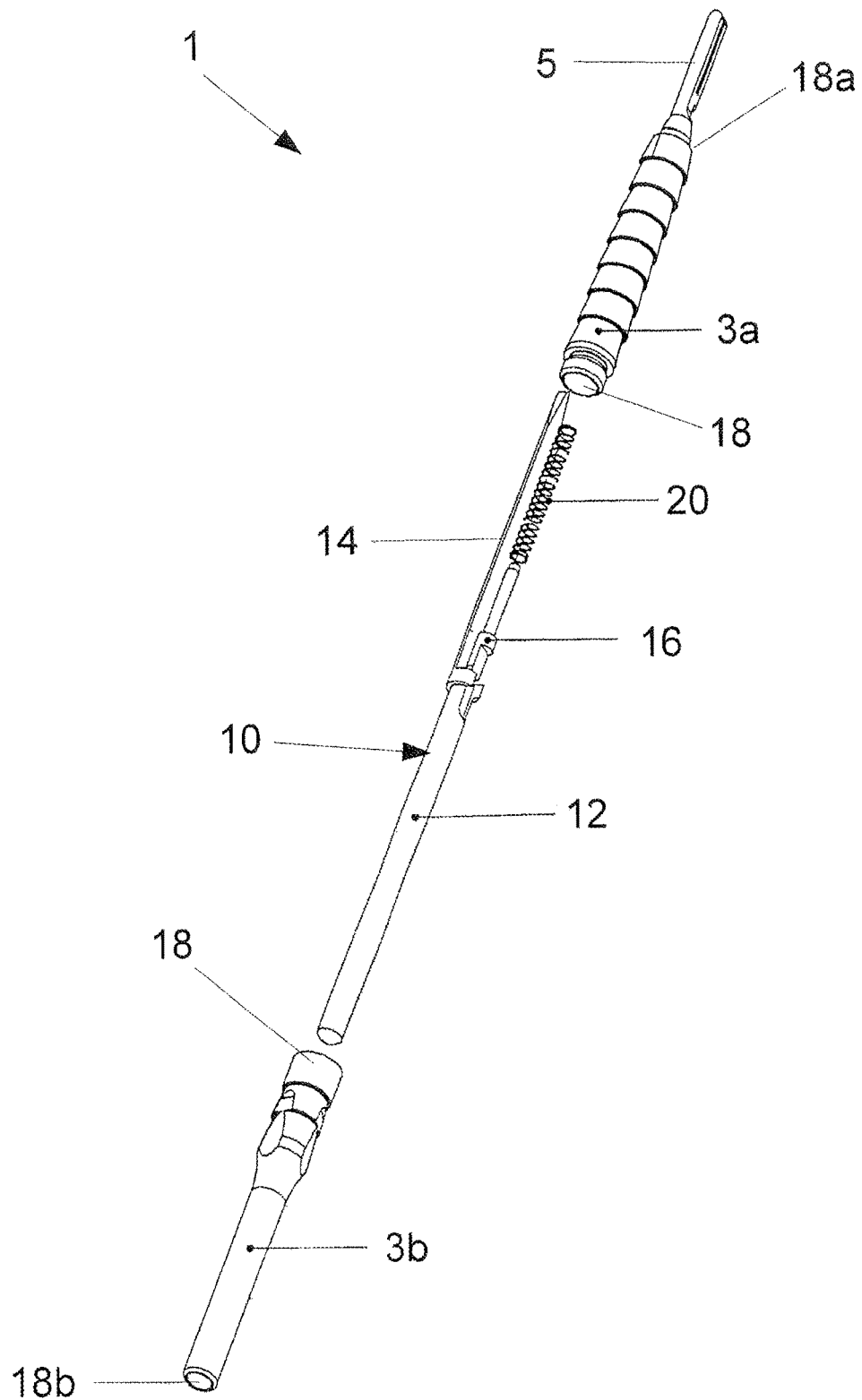
FIG. 1 is a line drawing evidencing an exploded illustration of one embodiment of a multi-piece scalpel holder.

The present invention proposes a scalpel holder, which has a grip piece, and a blade holder which is connected to the grip piece for the purpose of receiving a scalpel blade and holding the same fixed. The grip piece has a longitudinal axis and extends in the direction of this longitudinal axis—or in other words in a straight line in the longitudinal direction—and the blade holder is fastened on the front end of the grip piece.

The invention solves the problem by a configuration wherein the grip piece has a slider guide running substantially in the direction of the longitudinal axis and/or in the longitudinal direction of the grip piece, wherein a slider received in said slider guide is guided in a movable manner therein.

The slider in this case has a slider rod and a push rod, which are either fixed to each other, and/or can also be designed as a single piece together.

If the slider guide is designed as a single piece with the grip piece, this has the advantage that the direction of the slider guide is unambiguously and unchangeably prespecified relative to the grip piece. The slider guided in the slider guide can therefore be guided precisely in the direction of the scalpel blade such that it can push out the scalpel blade from the blade holder if it has no additional play.

According to the invention, the push rod has an end piece with a wedge-shaped design for this purpose, to lift out a scalpel blade fastened on the blade holder, and preferably an edge region constructed on the blunt end of the wedge-shaped end piece, for the purpose of pushing out the scalpel blade which has been lifted out of the blade holder.

According to the invention, the slider guide of the scalpel holder is arranged on the grip piece in such a manner that the wedge-shaped end piece of the slider, the same guided in the slider guide in the direction of the blade holder, slides past the scalpel blade, and lifts the scalpel blade out of the blade holder in the process. The push rod in this case advantageously glides along on a narrow side of the blade holder. In this way, the guiding of the slider in the slider guide is additionally stabilized, which enables a more exact guidance of the push rod.

The scalpel blade is elastically tensioned and fixed in the blade holder. For this purpose, the blade holder preferably has a locking part to hold the scalpel blade fixed, and preferably at least one guide groove for the purpose of receiving and guiding the scalpel blade.

The scalpel blade advantageously has a locking part opening corresponding to the locking part of the blade holder, for the purpose of receiving the scalpel blade in the locking part of the blade holder and holding the scalpel blade fixed; and it particularly preferably has a guide opening which corresponds with the guide groove of the blade holder and which forms a blade opening together with the locking part opening for the purpose of receiving and guiding the scalpel blade, and holding the same by means of clamping.

The scalpel blade fastened in the blade holder of the scalpel holder is locked in the locking part of the blade holder by means of its locking part opening. The edge of its guide opening simultaneously engages in the guide groove of the blade holder. The scalpel blade is therefore simultaneously received in the guide groove in a guided manner. If the scalpel blade is to be removed by the blade holder, it must therefore first be lifted off of the locking part. Only after this lifting can it further slide along the guide groove toward the front end of the blade holder, and then be ejected from the blade holder.

For this purpose, the edge region is advantageously arranged on the push rod—for the purpose of pushing off the scalpel blade which has been lifted out of the blade holder—in such a manner that the edge region, while contacting a narrow side of the scalpel blade, pushes the scalpel blade off of the blade holder, said scalpel blade having been lifted out, if the slider is further guided in the direction of the blade holder.

The grip piece can be designed as a single piece together with the blade holder; however, as an alternative, it can also be connected to the blade holder via, by way of example, a bolted connection or a bayonet connection.

If the grip piece is designed as a single piece together with the blade holder, this has the advantage that the grip piece and the blade holder are not able to move relative to each other. The surgeon can then guide the instrument precisely and exactly. If the grip piece is connected to the blade holder via a bolted connection or a bayonet connection, the grip piece and the blade holder can be adapted to given requirements and combined with each other in a modular manner.

The slider preferably has an actuating region by means of which the push rod can be actuated in the direction of the blade holder for the purpose of removing a scalpel blade fastened on the blade holder. The actuating region can be, by way of example, an actuating element arranged laterally or also proximally on the slide, by means of which the slider can be moved back and forth in the slider guide.

On the other hand, the actuating region can also be the rear end of the slider, by way of example, if the slider is sufficiently long and the end of the slider, which is opposite the push rod, projects sufficiently far out of the slider guide.

In this manner, the scalpel blade can be removed from the blade holder using only one hand, without this single hand coming near to the scalpel blade. The risk of injury as a result is very low. The scalpel holder can be easily accepted by a receptacle for used scalpel blades, and the actuating element or the actuating region is actuated, allowing the scalpel blade to be ejected into the receptacle.

In order to automatically retract the slider back into its starting position, the slider can have a return spring, by way of example.

The return spring can be arranged in this case around the slider rod or around a grip piece fastened to the slider, by way of example. Such a grip piece can be guided, by way of example, in a guide sleeve preferably configured with a bore hole passing through the same, said guide sleeve being connected to the grip piece and holding the grip piece in a manner allowing movement. A bore hole which passes through the guide sleeve enables a simpler sterilization of the used element.

The return spring is advantageously arranged sitting on the guide sleeve. As such, the slider can be more precisely guided on the slider guide, because it is still additionally guided in a guide sleeve.

In order to rule out an accidental actuation of the slider, the same can have an arrester. The arrester can be designed, by way of example, in such a manner that a rotation of the slider about its longitudinal axis holds the slider fixed in its current position, and prevents an accidental sliding of the slider in the slider guide. If the slider is again rotated back into its original position, it can be actuated again in the longitudinal direction of the grip piece. In addition to this design of the arrester, many other designs are known to a person skilled in the art—for example in the form of a sleeve nut, a locking lever, or the like.

In one preferred embodiment of a scalpel holder, the grip piece is hollow and the slider guide is arranged running inside the grip piece. The grip piece in this case is moved through the grip piece in the direction of the blade holder, which enables a compact construction.

For this purpose, the hollow grip piece advantageously has a first passage on its front end—meaning on its end which faces the blade holder, or also the distal end—and a second passage on its rear end—meaning its end which faces away from the blade holder, or also the proximal end—for the purpose of the slider passing through the same.

The slider is advantageously held in the slider guide in this case in such a manner that the end of the slider which is opposite the push rod projects out of the passage arranged on the rear end of the grip piece, and forms the actuating region of the slider.

A scalpel holder designed in this manner can be actuated in a particularly simple manner using one hand: by pressing on the rear end of the slider, similarly to a retractable ballpoint pen, the scalpel blade can be quickly removed from the blade holder.

The grip piece—particularly if it has a hollow design—has at least two grip piece parts, which can be connected to each other. This enables a simple cleaning and sterilization of the used scalpel holder. The at least two grip piece parts can be connected to each other by means of bolted connections, plug connections, or bayonet connections, by way of example, thereby forming the grip piece.

The invention is described below with reference to a preferred embodiment, without being thereby restricted to this embodiment. The features of the embodiment can particularly be freely combined or substituted with other features to the extent these are compatible.

The indications used in the embodiment—such as above, below, left and right, and the like—refer to the embodiment, and should not be understood as any manner of restriction.

DETAILED DESCRIPTION OF THE FIGURES

FIG. 1 shows a scalpel blade 1 consisting of multiple parts, having a first grip piece part 3*a* and a second grip piece part 3*b*, which together form the grip piece 3.

The first grip piece part 3*a* and the second grip piece part 3*b* have a hollow construction and can be bolted together to form the grip piece 3. The first grip piece part 3*a* is fixed to a blade holder 5 for the purpose of receiving a scalpel blade 7 and holding the same fixed. A slider 10 guided through the interior of the hollow grip piece 3 has a slider rod 12, a push rod 14 connected to the slider rod 12, and a guide pin 16 which is likewise connected to the slider rod 12.

The first grip piece part 3*a* has a first passage 18*a* on its end, which faces toward the blade holder 5, for the purpose of guiding the push rod 14 through the first grip piece part 3*a*. The rear end of the slider 10 which faces away from the push rod 14 projects through a second passage 18*b* configured on the rear end of the second grip piece part 3*b* when the first grip piece part 3*a* is bolted together to the second grip piece part 3*b*. The first passage 18*a* and the second passage 18b are parts of a slider guide 18 which runs in the interior of the hollow grip piece 3, wherein the slider 10 is guided in said slider guide 18. The guide pin 16 connected to the slider rod 12 is surrounded by a return spring 20 which sits on a guide sleeve which is arranged in the interior of the first grip piece part 3a, which is fixed to the same, and which is not illustrated in further detail. The guide sleeve has a through boring. The guide pin 16 is guided in the passage of the guide sleeve in a movable manner.

The slider rod 12 of the slider 10 has an actuating region 22 on its rear end. The slider 10 is arranged in a movable manner in the interior of the grip piece 3, inside the slider guide 18, the opening 18a, the passage 18b, and the guide sleeve arranged in the interior of the first grip piece part 3a.

As a result of pressure on the actuating region 22, the slider 10 is slid forward by means of the push rod 14, through the first passage 18a and along the blade holder 5, and can—as described below—remove the scalpel blade 7 which is received and fixed in the blade holder 5.

Figure 2:
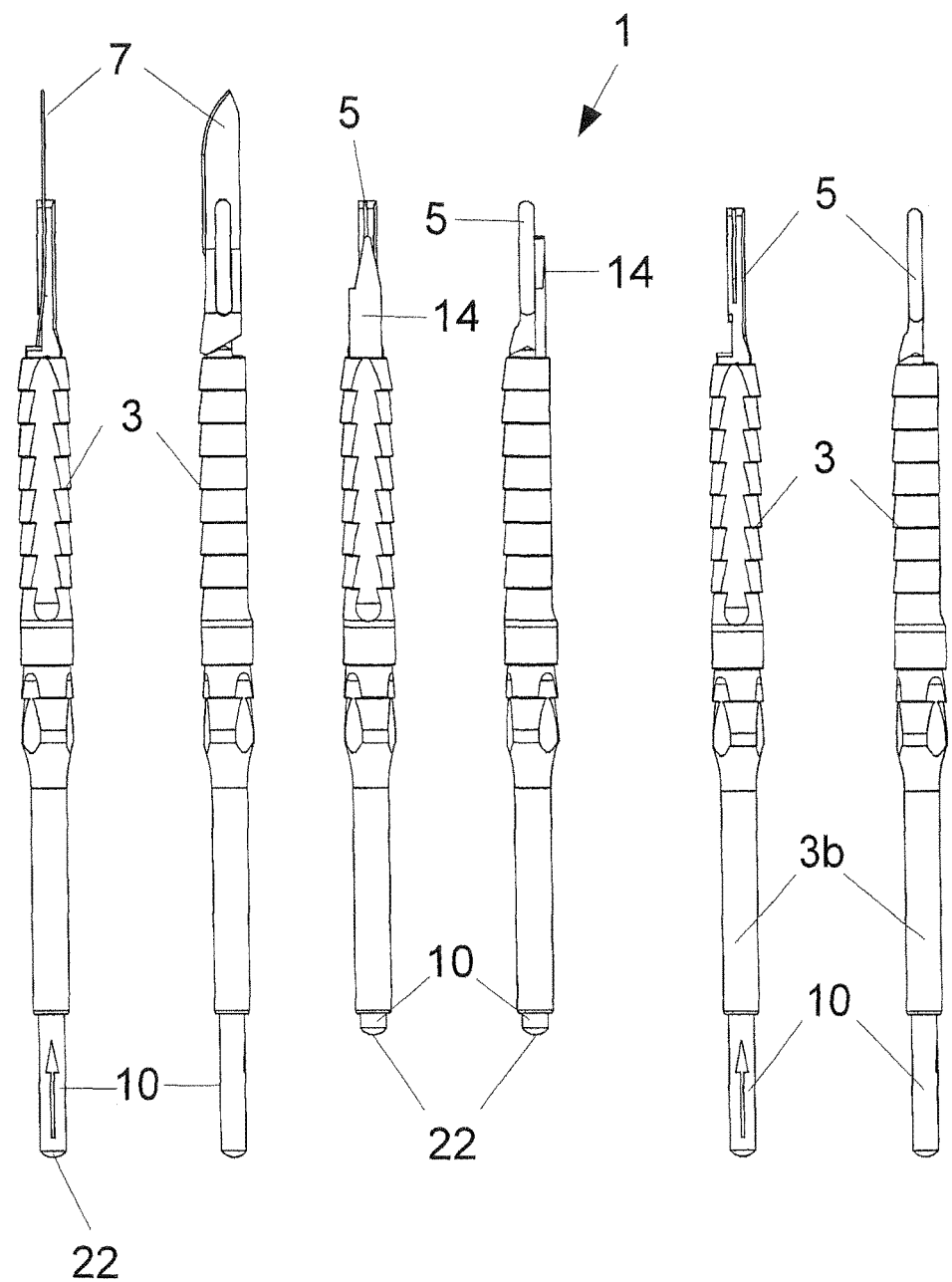
FIG. 2 is a line drawing evidencing multiple side views of the scalpel holder in FIG. 1, with and without scalpel blades.

FIG. 2 shows the scalpel holder 1 in different views. The two figures at left show the scalpel holder 1 with the scalpel blade 7 in-place, as a top view of a narrow side of the scalpel blade 7, and as a top view of a wide side of the scalpel blade 7. The slider 10 is slid to the rear and is in its starting position.

The two central figures show the scalpel holder 1 with the blade already removed. The slider 10 is slid forward and has slid the push rod 14 forward through the first passage 18a along the blade holder 5, and has lifted the scalpel blade 7 off of the blade holder 5.

The two figures at right show the scalpel holder 1 after the return spring 20 has pushed the slider 10 back into its starting position. This occurs as soon as there is no longer any pressure exerted on the actuating region 22. At this point, the blade holder 5 is again ready to receive a new scalpel blade 7.

Figure 3:
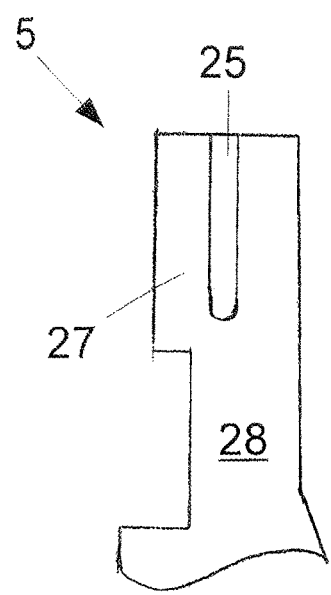
FIG. 3 is a line drawing evidencing a side view of a blade holder for the scalpel holder in FIGS. 1 and 2.

FIG. 3 shows the blade holder 5 in a side view: the blade holder 5 has two guide grooves 25 which run longitudinally and which are positioned opposite each other, for the purpose of receiving and guiding the scalpel blade 7, and has a locking part 27 for the purpose of holding the scalpel blade in a fixed manner. The scalpel blade 5 further has a glide surface 28, wherein the push rod 14 can be guided in a gliding manner on the same.

Figure 4:
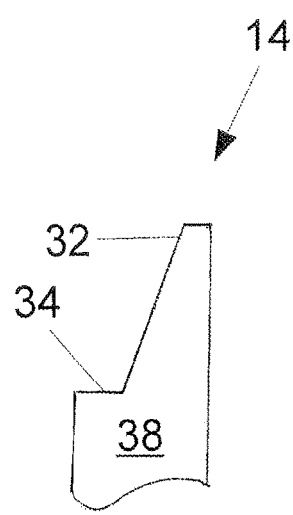
FIG. 4 is a line drawing evidencing a top view of the front portion of a push rod.

FIG. 4 shows the lateral top view of the front end of the push rod 14. The push rod 14 has an end piece 32 with a wedge-shaped design, for the purpose of lifting off the scalpel blade 7 fastened in the blade holder 5 from the locking part 27, and has an edge region 34 constructed on the blunt end of the wedge-shaped end piece 32, for the purpose of pushing off the scalpel blade 7 which has been lifted off from the blade holder 5, along the two guide grooves 25 which run longitudinally opposite each other. The end of the push rod 14 which is opposite the front end 38 in this case glides along the glide surface 28 of the blade holder 5, from the bottom to the top, and initially lifts off the scalpel blade 7 placed on the locking part 27 by the action of the wedge-shaped end piece 32 engaging behind the scalpel blade 7. During the further sliding of the push rod 14 upward, the edge 34 catches the rear narrow side 40 of the scalpel blade 7 and presses the scalpel blade 7 guided in the guide grooves 25 of the blade holder 5 out of the blade holder 5.

Figure 5:
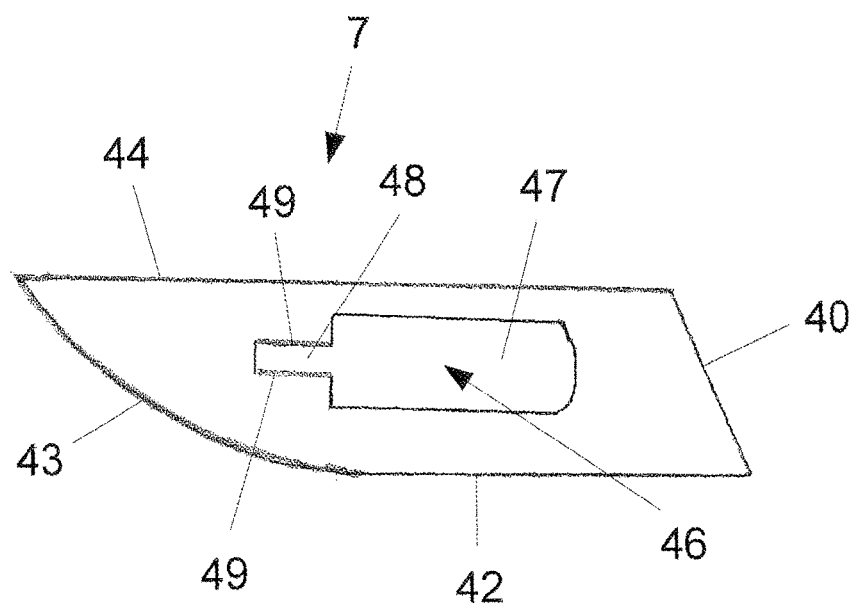
FIG. 5 is a line drawing evidencing a scalpel blade to be placed in the blade holder in FIG. 3.

FIG. 5 shows the scalpel blade 7. The scalpel blade 7 has a cutting side 42 and a cutting edge 43 configured on the cutting side 42, as well as a blade heel 44. The blade opening 46 removed from the wide side of the scalpel blade 7 consists of a locking part opening 47 for the purpose of receiving the scalpel blade in the locking part 27 of the blade holder 5 and holding the same fixed, as well as a guide opening 48 which is bounded by two shanks 49 positioned opposite each other. When the scalpel blade 7 is placed in the blade holder 5, the two shanks 49 of the scalpel blade 7 are slid into the guide groove 25 of the blade holder 5, and are further slid in the direction of the grip piece until the locking part opening 47 of the scalpel blade 7 locks into the locking part 27 of the blade holder 5. In this way, the scalpel blade 7 is connected to the blade holder 5 in a clamped and fixed manner.

If the scalpel blade 7 is intended to be removed from the blade holder 5 following use, it must first be lifted by its rear narrow side 40 which faces the grip piece before it can be moved over the locking part 27 and removed. This problem is solved by the push rod 14 described here, when the push rod 14 slides forward.

LIST OF REFERENCE NUMBERS 1 scalpel holder
3 grip piece
3a first grip piece part
3b second grip piece part
5 blade holder
7 scalpel blade
10 slider
12 slider rod
14 push rod
16 guide pin
18 slider guide
18a first passage
18b second passage
20 return spring
22 actuating region
25 guide grooves
27 locking part
28 glide surface
32 end piece
34 edge region
38 front end of the push rod
40 rear narrow side
42 cutting side
43 cutting edge
44 blade heel
46 blade opening
47 locking part opening
48 guide opening
49 shank The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

I claim:

1. A scalpel holder, having a grip piece with a longitudinal direction and a blade holder which is connected to the grip piece and which blade holder functions to receive a scalpel blade and hold the same fixed, wherein the grip piece has a slider guide running substantially in the longitudinal direction of the grip piece, wherein a slider received in said slider guide is movably guided in the slider guide, wherein the slider has a slider rod and a push rod connected to each other in a fixed manner, and the push rod furthermore has an end piece with a wedge-shaped design for the purpose of allowing a person using only one hand to engage the push rod, thereby lifting out a scalpel blade fastened on the blade holder, wherein the slider guide is arranged on the grip piece in such a manner that the end piece of the slider guided in the slider guide in the direction of the blade holder slides past the scalpel blade while lifting the scalpel blade out of the blade holder, and wherein the push rod is divided in cross-section into two components, a first component comprising a shoulder edge region, and a second component comprising the wedge-shaped end piece extending longitudinally beyond the first component, for the purpose of laterally lifting the scalpel blade away from the blade holder while simultaneously pushing the scalpel blade longitudinally away from the blade holder.

2. The scalpel holder of claim 1, wherein the slider rod is designed as a single piece together with the push rod.

3. The scalpel holder of claim 1, wherein an edge region functions to push off the scalpel blade after such blade has been lifted out of the blade holder, is arranged on the push rod in such a manner that such edge region, while contacting a narrow side of the scalpel blade, pushes off the scalpel blade from the blade holder, said scalpel blade having been lifted off, when the slider is further guided in the direction of the blade holder.

4. The scalpel holder of claim 1, wherein the slider guide is designed as a single piece together with the grip piece.

5. The scalpel holder of claim 1, wherein the grip piece is designed as a single piece together with the blade holder.

6. The scalpel holder of claim 1, wherein the slider has an actuating region in the form of an actuating element arranged laterally or proximally on the slider, for the purpose of actuating the slider.

7. The scalpel holder of claim 1, wherein the slider has a return spring.

8. The scalpel holder of claim 7, wherein the return spring is arranged around the slider rod or around a guide pin fastened to the slider.

9. The scalpel holder of claim 8, wherein the guide pin is guided in a guide sleeve, and held in the same in a movable manner, said guide sleeve being connected to the grip piece and configured with a bore hole passing through the same, and the return spring is arranged sitting atop the guide sleeve.

10. The scalpel holder of claim 1, wherein the grip piece is hollow, and the slider guide is arranged running inside of the grip piece.

11. The scalpel holder of claim 10, wherein the grip piece has a first passage on a distal end of such grip piece, and a second passage on a proximal end of such grip piece, for the purpose of guiding the slider through the same.

12. The scalpel holder of claim 1, wherein a part of the slider projects from a rear end of the grip piece, and forms an actuating region of the slider.

13. The scalpel holder of claim 1, wherein the grip piece has at least two grip piece parts, which can be connected to each other.

14. The scalpel holder of claim 13, wherein the at least two grip piece parts are connected to each other by means of bolted connections, plug connections, or bayonet connections, in a detachable manner.

15. The scalpel holder of claim 1, further comprising wherein the slider has an arrester to protect against unintentional actuation of the slider.

16. The scalpel holder of claim 1, further comprising wherein the scalpel blade is elastically tensioned and the blade holder comprises a locking part and at least one guide groove to hold the scalpel blade fixed.

* * * * *